(12) United States Patent
Debutts

(10) Patent No.: US 8,946,123 B2
(45) Date of Patent: Feb. 3, 2015

(54) COMPOSITIONS AND METHODS FOR CONTROLLING THE DIRECTION OF GROWTH OF PLANTS WITH ROOTLETS

(76) Inventor: Richard Foster Debutts, Smyrna, GA (US)

( * ) Notice: Subject to any disclaimer, the term of this patent is extended or adjusted under 35 U.S.C. 154(b) by 617 days.

(21) Appl. No.: 12/472,576

(22) Filed: May 27, 2009

(65) Prior Publication Data

US 2009/0298692 A1    Dec. 3, 2009

Related U.S. Application Data

(60) Provisional application No. 61/056,453, filed on May 28, 2008.

(51) Int. Cl.
| A01N 47/10 | (2006.01) |
| A01N 37/10 | (2006.01) |
| A01P 13/00 | (2006.01) |
| A01N 57/20 | (2006.01) |
| A01N 37/18 | (2006.01) |
| A01N 65/00 | (2009.01) |

(52) U.S. Cl.
CPC ............... *A01N 57/20* (2013.01); *A01N 37/18* (2013.01); *A01N 65/00* (2013.01)
USPC .......................................... 504/135; 504/144

(58) Field of Classification Search
CPC ... A01N 37/18; A01N 65/00; A01N 2300/00; A01N 25/10; A01N 25/24; A01N 57/20
USPC ................................................... 504/135, 144
See application file for complete search history.

(56) References Cited

U.S. PATENT DOCUMENTS

| 3,920,436 | A | 11/1975 | Janssen |
| 4,088,473 | A | 5/1978 | Linton |
| 4,882,874 | A | 11/1989 | Paulson et al. |
| 5,744,423 | A * | 4/1998 | Voris et al. ..................... 504/361 |
| 5,750,130 | A | 5/1998 | Ferrell et al. |
| 6,001,346 | A | 12/1999 | Delwiche et al. |
| 6,528,114 | B1 | 3/2003 | Summons |
| 6,676,954 | B2 | 1/2004 | Dai et al. |
| 7,094,734 | B2 | 8/2006 | Ushiguchi et al. |
| 7,264,796 | B2 | 9/2007 | Hejna et al. |
| 2002/0034550 | A1 * | 3/2002 | Quong .......................... 424/489 |
| 2003/0215657 | A1 | 11/2003 | Tijsma et al. |
| 2006/0040827 | A1 | 2/2006 | Rajamannan |
| 2007/0110783 | A1 | 5/2007 | Pildysh |
| 2007/0238615 | A1 | 10/2007 | Krause et al. |

OTHER PUBLICATIONS

Nakajima-Kambe et al., Applied Microbiology and Biotechnology vol. 51, No. 2, 134-140.*

* cited by examiner

*Primary Examiner* — Janet Epps-Smith
*Assistant Examiner* — Courtney Brown
(74) *Attorney, Agent, or Firm* — Gardner Groff Greenwald & Villanueva, PC

(57) ABSTRACT

Described herein are compositions including an herbicide, a capsaicinoid, and an acrylic for controlling the direction of growth of plants with rootlets. Also described herein are methods for making and using the compositions.

16 Claims, 3 Drawing Sheets

COMPOSITIONS AND METHODS FOR CONTROLLING THE DIRECTION OF GROWTH OF PLANTS WITH ROOTLETS

CROSS REFERENCE TO RELATED APPLICATION

This application claims priority upon U.S. provisional application Ser. No. 61/056,453, filed May 28, 2008. This application is hereby incorporated by reference in its entirety.

BACKGROUND

In temperate climates, vine control typically proves difficult during the spring and summer months. This problem persists throughout the year in warmer, sub-tropical and tropical climates. Even in temperate climates, numerous species of vines grow throughout the year; thus presenting a dilemma for surfaces on which they grow. These vines may damage a home's bricks, brick mortar, eaves, soffits, moldings, sidewalks, and may potentially overcome and kill trees. With current herbicidal formulations, repeated applications and constant grooming is required to maintain a pleasing, well manicured lawn, sidewalks, trees, and home.

As stated above, currently available herbicidal formulations represent a limited option for maintaining the appearance of a home, sidewalks, trees, and lawn. The development of a more efficient, durable, and viable formulations that control vine growth and other plants with rootlets is eagerly awaited.

BRIEF DESCRIPTION OF THE DRAWINGS

The accompanying drawings, which are incorporated in and constitute a part of this specification, illustrate several aspects described below.

SUMMARY

Figure 1:
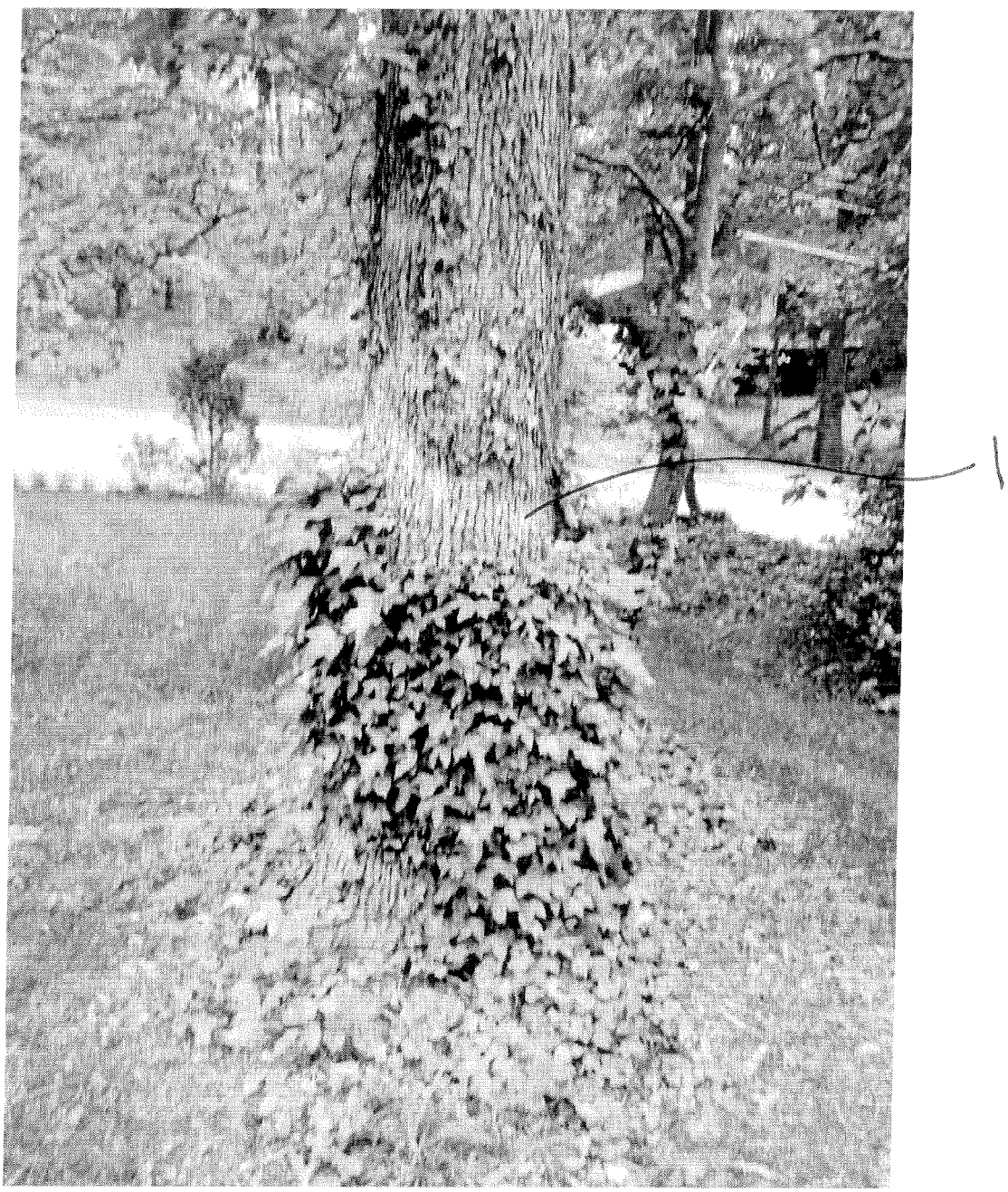
FIGS. 1 and 2 show the ability of a composition described herein to redirect ivy growth on a tree.

Described herein are compositions including an herbicide, a capsaicinoid, and an acrylic for controlling the direction of growth of plants with rootlets. Also described herein are methods for making and using the compositions. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "an herbicide" includes mixtures of two or more such herbicides, and the like.

"Optional" or "optionally" means that the subsequently described event or circumstance can or cannot occur, and that the description includes instances where the event or circumstance occurs and instances where it does not. For example, the phrase "optionally shake" means that the composition may or may not be shaken.

Described herein are compositions having an herbicide, a capsaicinoid, and an acrylic. Each component is described below. Herbicides known in the art can be used herein. As will be discussed below, the herbicide when used in combination with the capsaicinoid does not kill the plant with rootlets but repels the plant. Although it is possible that the plant could be killed with the compositions described herein, the goal is not to kill the plant but to merely redirect the growth of the plant. Examples of such herbicides useful herein include, but are not limited to, prometon, picloram, pendimethalin, paraquat, simazine, sulfometuron methyl, tebuthiuron, triclopyr, monosodium methanearsonic acid, metsulfuron methyl, 2-methyl-4-chlorophenoxyacetic acid, isoxaben, imazapyr, hexazinone, glufosinate, foamine, fluridone, fluazifop-P-butyl, enothall, disodium methylarsonate, diuron, diquat, dihlobenil, dicamba, clpyralid, clethodihn, chlorosulfuron, bromoxynil, bromacil, amitrole, acrolein, glyphosate, or 2,4 dichlorophenoxyacetic acid.

In one aspect, the herbicide includes glyphosate or the salt thereof. Examples of glyphosate based herbicides include, but are not limited to Gly Star™ Pro, Ortho® Total Vegetation Weed Killer. In other aspects, non-glyphosate herbicides such as, for example, Ortho's "Total Vegetation Killer," can be used herein and contains prometon/pramitol. In one aspect, the herbicide is approximately 5% to 40% weight per volume, 10% to 30% weight per volume, 20% to 30% weight per volume, 5% to 15% weight per volume, 5% to 10% weight per volume, 6% to 10% weight per volume, 7% to 9% weight per volume, or about 8% weight per volume of the composition.

Capsaicinoids are a class of compounds produced as a secondary metabolite by chili peppers. Capsaicin is the main capsaicinoidl in chili peppers, followed by dihydrocapsaicin. Other examples of capsaicinoids include nordihydrocapsaicin, homodihydrocapsaicin, homlocapsaicin, and nonivamide. When used in combination with the herbicide, the compositions described herein repel plants with rootlets. In one aspect, the capsaicinoid is approximately 0.1% to 20% weight per volume, 0.5% to 15% weight per volume, 1% to 10% weight per volume, 1% to 5% weight per volume, 1% to 3% weight per volume, or about 2% weight per volume of the composition. The capsaicinoids useful herein can be water base or oil base, and can be naturally-derived compounds or synthetic compounds. In one aspect, the capsaicinoid can be Red Savina habanero, Dorset Naga, Naga Jolokia, or Nordihiydrocapsaicin. In another aspect, the capsaicinoid is Pepper Foam manufactured by Mace.

The acrylic is used to encapsulate the herbicide and capsaicinoid as well as adhere the composition to the substrate. Not wislhing to be bound by tlleory, it is believed that the amount of acrylic used is sufficient to produce a soft coating such that when the rootlets of the plant contact with (e.g., penetrate) the coating they are exposed to the herbicide and capsaicinoid. Thus, when the acrylic is used in the appropriate amounts, a relatively thick composition is produced that can be readily applied to a substrate.

The acrylic useful herein can be any polymer useful in forming adhesives and the like. In certain aspects, two or more acrylics can be used. In one aspect, the acrylic can be derived form acrylic acids or esters, and methacrylates (acids and esters) as well. In other aspects, the acrylic can be styrene butadiene, acrylic homopolymers, acrylic copolymers, acrylonitrile butadiene, polychloroprene, vinyl acetates, ethylene vinyl acetate copolymers and carboxylated styrene butadiene. Homopolymers and copolymers are useful herein. Thus, the acrylic can be the polymerization product between unsaturated monomers such as, for example, vinyl compounds (e.g., acetates, alcohol, chloride) and the acrylic monomer. Depending upon the selection of the acrylic, the acrylic can impart waterproofing properties to the composition. The acrylic can also facilitate the adhesion of the composition to a substrate. In one aspect, the acrylic is a water-base(d composition such as Acrylic Mortar Mix manufactured by Custom Building Products, which is a water-based acrylic suspension. Other acrylics useful in preparing mortars can be used as well including Golden Open Acrylic and Polymer Medium (gloss) both manufactured by Golden Artists, Inc. In one aspect, the acrylic is approximately 60% to 90%, 65% to 85% weight per volume, 65% to 80% weight per volumne, 65% to 75% weight per volume, or about 70% weight per volume of the composition.

An optional component that can be used in the compositions described herein includes water-based polyurethanes. Examples of water-based polyurethanes include, but are not limited to, a polyester polyurethane, an aliphatic polyester polyurethane, an aliphatic polyurethane, and the like. Thie polyurethanes can have groups that can readily be deprotonated (e.g., sulfonate) or protonated (e.g., amine) to stabilize the polyurethane in water. Examples of water-based polyurethanes include, but are not limited to, Behr Premium Plus with Style Crystal Clear Water Based Polyurethane, Cabot® Water Based Polyurethane Varnish, Minwax® VOC Water Based Polyurethane, or Minwax® Polycrylic Protective Finish/Clear Satin. In one aspect, the polyurethane is approximately 5% to 40% weight per volume, 10% to 30% weight per volume, 15% to 25% weight per volume, or about 20% weight per volume of the composition.

Also described herein are methods of making the compositions by mixing an herbicide, capsaicinoid, and an acrylic. In one aspect, the acrylic and herbicide are mixed together first, followed by the addition of the capsaicinoid. Not wishing to be bound by theory, the acrylic encapsulates the herbicide and capsaicinoid. The amount of acrylic provides a consistency that is not too watery yet not so thick that it is difficult to apply to a substrate. As a result of this encapsulation, the herbicide and capsaicinoid do not leach out at an appreciable rate, which means that the compositions are not harmful to trees if the composition is applied to such a substrate. It is desirable to use an effective amount of herbicide and capsaicinoid such that these components do not demulsify and separate from the composition. The compositions are stable and can be stored for extended periods of time at room temperature.

Figure 2:
Figure 3:
FIG. 3 shows the ability of a composition described herein to redirect ivy growth on the exterior surface of a house.

The compositions useful herein can prevent the growth by a plant having rootlets on a surface. The term n"rootlet" as used herein include plants with aerial rootlets, tendrils with or without adhesive discs, and the like. The compositions described herein do not kill the plaint (or at most kill a minor amount). Not wishing to be bound by theory, when the plant comes into contact with the composition and the rootlets penetrate the composition, the rootlets interact with the capsaicinoid and "burn" the rootlets. This results in redirecting the growth of the plant away from the treated substrate. An example of this is depicted in FIGS. 1 and 2. In FIGS. 1 and 2, a composition as described herein was applied to the bark of a tree and the ivy was allowed to grow for three months. The white line 1 indicates where the composition was applied to the tree. As shown in FIGS. 1 and 2, the ivy did not grow above the application line 1. FIG. 3 shows the ability of the compositions described herein to redirect ivy growth on the exterior surface of a house. As shown in FIG. 3, when a composition described herein is applied to house, well-defined lines of ivy can be produced. Examples of plants with rootlets include, but are not limited to, ivy (e.g., English Ivy, Boston Ivy, Grape Ivy), Virginia Creeper, Creeping Fig, Climbing Hydrangea, Trumpet Creeper, Grape Ivy, or a species of *Cissus*.

Any substrate where plants with rootlets grow can be treated with the compositions described herein. In one aspect, the substrate can be a porous material such as, for example, brick, mortar, stucco, concrete, fiber concrete siding, wood, or tree trunks. In another aspect, the compositions can be applied to trees, particularly the bark of trees where plants with rootlets typically grow (see for examples FIGS. 1 and 2). As discussed above, the compositions described herein do not harm trees. The compositions can be applied to a substrate using techniques in known the art: including, but not limited to, brushing, spraying, rolling, and the like. In certain aspects, the composition is applied to the substrate when the atmospheric temperature is greater than 55° F. In certain aspects, it is desirable that once the coating is applied to the substrate and subsequently dried, a clear coat is formed. This is desirable in residential applications and when applied to trees. Multiple coats can be applied as needed. In certain aspects, the composition once applied to the substrate can redirect plant growth up to six months, 12 months, 18 months, or 24 months.

The compositions and methods described herein provide a number of advantages when compared to prior art formulations. The compositions and methods provide a preventative measure from damage caused by plants with rootlets. For example, the compositions described herein can be applied around exterior windows eaves, molding, soffits and anywhere where plants with rootlets grow (e.g., vines) and cause damage. By preventing such growth, costly repairs can be avoided. Alternatively, mortar can be damaged by intrusive vines such as ivy. When removing vines, mortar is removed where the vine was attached. Over several years this could destabilize bricks and require repair. The compositions described herein can prevent this from happening.

The compositions described herein can protect trees from long-term exposure to vines and other plants with rootlets. Vine-clad trees can look attractive but over time the vines can take over the tree and choke it. Vines such as ivy weaken trees by keeping the bark damp and blocking sunlight. Finally, vines add weight to trees, making them top heavy and susceptible to falling. In one aspect, by applying a ring four feet up the tree with the compositions described herein, it is possible to produce greenery around the trunk yet keep the tree healthy.

The removal of vines and other plants with rootlets can be a time-consuming project and labor-intensive. Additionally, the removal of vines and other plants can involve the use of ladders, which creates safety concerns. The compositions described herein avoid these drawbacks by redirecting plant growth. Moreover, the composition need only be applied periodically (e.g., every two years), which provides significant convenience.

Finally, the compositions described herein can control the spread of mosquitoes and other harmful insects. After mosquitoes hatch they look for the most humid places around a yard to roost and rest. Ivy present of the ground provides a humid environment. Thus, by controlling the direction of ivy and other plants with rootlets, it is possible to control the population of mosquitoes and other insects.

EXAMPLES

The following examples are put forth so as to provide those of ordinary skill in the art with a complete disclosure aid description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

First, 150 mL Acrylic Mortar Mix manufactured by Custom Building Products was mixed with 35 mL of water based polyurethane (Minwax® Water Based Polyurethane for Floors). Second, 10 mL of a glyphosate based herbicide (Gly Star™ Pro) and 5 mL capsaicin (Defender Pepper Spray) were added to the acrylic/water based polyurethane mixture. To mix thoroughly, the ingredients were shaken vigorously. This composition had little odor. Next, the composition was applied to a surface using either a brush, roller, or spraying device. This weather resistant chemical formulation was evenly applied at a temperature of 55° F. or higher. The treated surface dried for approximately two hours, and if desired, a second coat was applied. This composition dried clear. Then the composition was stored at approximately 72° F.

Example 2

First, 8 oz. Acrylic Mortar Mix manufactured by Custom Building was mixed with 3 oz. Golden Mediums, Polymer Medium((Gloss), made by Golden Artist Colors, Inc. Next, 4 oz glyphosate based herbicide (Gly Star Pro) was stirred into the acrylic mix. Finally, 1 oz of Mace brand Pepper Foam was added and mixed to produce the final formulation.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary

What is claimed:

1. A composition consisting of an herbicide, capsaicin, and an acrylic, wherein the composition consists of an emulsion that prevents the growth by a plant comprising rootlets on a surface.

2. The composition of claim 1, wherein the herbicide comprises prometon, picloram, pendimethalin, paraquat, simazine, sulfometuron methyl, tebuthiuron, triclopyr, monosodium methanearsonic acid, metsulfuron methyl, 2-methyl-4- chlorophenoxyacetic acid, isoxaben, imazapyr, hexazinone, glufosinate, foamine, fluridone, fluazifop-P-butyl, enothall, disodium methylarsonate, diuron, diquat, dihlobenil, dicamba, clpyralid, clethodim, chlorosulfuron, bromoxynil, bromacil, amitrole, acrolein, 2,4 dichlorophenoxyacetic acid, or any combination thereof.

3. The composition of claim 1, wherein the herbicide comprises glyphosate or the salt thereof.

4. The composition of claim 1, wherein the herbicide is approximately 5% to 20% weight per volume, the capsaicin is approximately 0.1% to 20% weight per volume, and the acrylic is approximately 65% to 85% weight per volume of the entire composition.

5. A method for preventing growth by a plant comprising rootlets on a surface comprising applying to the surface the composition of claim 1.

6. The method of claim 5, wherein the plant comprises vines with rootlets.

7. The method of claim 5, wherein the plant comprises English Ivy, Boston Ivy, Creeping Fig, Poison Ivy, Virginia Creeper, Climbing Hydrangea, Trumpet Creeper, Grape Ivy, a species of *Cissus*, or any plant species that uses rootlets to attach and grow on a surface.

8. The method of claim 5, wherein the composition is applied to the surface by brushing the composition onto the surface.

9. The method of claim 5, wherein the composition is applied to the surface by spraying the composition onto the surface.

10. The method of claim 5, wherein the composition is applied the surface by rolling the composition onto the surface.

11. The method of claim 5, wherein the surface is porous.

12. The method of claim 5, wherein the surface comprises brick, mortar, stucco, concrete, fiber concrete siding, wood, or tree trunks.

13. The method of claim 5, wherein composition has been applied to the surface and subsequently dried, the dried composition is clear.

14. The composition of claim 1, wherein the acrylic is a water-based acrylic suspension.

15. The composition of claim 1, wherein the capsaicin is water-based or oil based composition.

16. The composition of claim 1, wherein the herbicide is a compostion consisting of a glyphosate salt and one or more inert ingredients.

* * * * *